US012755135B2

(12) United States Patent
Kumar et al.

(10) Patent No.: US 12,755,135 B2
(45) Date of Patent: Oct. 6, 2026

(54) ATTENTION-BASED MACHINE LEARNING TECHNIQUES USING TEMPORAL SEQUENCE DATA AND DYNAMIC CO-OCCURRENCE GRAPH DATA OBJECTS

(71) Applicant: Optum, Inc., Minnetonka, MN (US)

(72) Inventors: Amit Kumar, Gaya (IN); Suman Roy, Bangalore (IN); Ayan Sengupta, Noida (IN); Paul J. Godden, London (GB)

(73) Assignee: Optum, Inc., Minnetonka, MN (US)

( * ) Notice: Subject to any disclaimer, the term of this patent is extended or adjusted under 35 U.S.C. 154(b) by 998 days.

(21) Appl. No.: 17/820,681

(22) Filed: Aug. 18, 2022

(65) Prior Publication Data

US 2024/0062052 A1 Feb. 22, 2024

(51) Int. Cl.
*G06N 3/049* (2023.01)
*A61B 5/00* (2006.01)
*G06F 16/901* (2019.01)

(52) U.S. Cl.
CPC ........... *G06N 3/049* (2013.01); *A61B 5/7267* (2013.01); *G06F 16/9024* (2019.01)

(58) Field of Classification Search
CPC ........ G06N 3/049; G06N 3/044; G06N 3/045; G06N 3/08; G06N 5/022; A61B 5/7267; G06F 16/9024; G16H 10/60; G16H 15/00; G16H 40/20; G16H 50/20; G16H 50/70
See application file for complete search history.

(56) References Cited

U.S. PATENT DOCUMENTS

| | | | |
|---|---|---|---|
| 8,019,582 | B2 | 9/2011 | Iliff |
| 10,566,093 | B2 | 2/2020 | O'Connor |
| 10,734,113 | B2 | 8/2020 | Tang et al. |
| 10,861,590 | B2 | 12/2020 | White et al. |
| 2010/0324938 | A1 | 12/2010 | Ennett et al. |
| 2014/0258306 | A1 | 9/2014 | Nunez et al. |

(Continued)

FOREIGN PATENT DOCUMENTS

| | | |
|---|---|---|
| CN | 111798954 A | 10/2020 |
| KR | 10-2225894 B1 | 3/2021 |

OTHER PUBLICATIONS

Ahmedt-Aristizabal, David et al. "Graph-Based Deep Learning For Medical Diagnosis and Analysis—Past, Present and Future," Sensors, vol. 21, No. 4758, Jul. 12, 2021, pp. 1-48, DOI: 10.3390/s21144758.

(Continued)

*Primary Examiner* — Hien L Duong
(74) *Attorney, Agent, or Firm* — Alston & Bird LLP

(57) ABSTRACT

Various embodiments of the present invention provide methods, apparatus, systems, computing devices, computing entities, and/or the like for generating a representative embeddings for a plurality of temporal sequences by using a graph attention augmented temporal network based at least in part on dynamic co-occurrence graphs for preceding temporal sequences and initial embeddings, where the dynamic co-occurrence graphs are projections of a global guidance co-occurrence graph on features of the preceding temporal sequences, and the initial embeddings are generated by processing a latent representation of corresponding features that is generated by a sequential long short term memory model as well as a feature tree using a tree-based long short term memory model.

20 Claims, 7 Drawing Sheets

(56) References Cited

U.S. PATENT DOCUMENTS

| | | | | |
|---|---|---|---|---|
| 2015/0154509 | A1* | 6/2015 | Lightner | G06F 16/22 706/12 |
| 2017/0262429 | A1* | 9/2017 | Harper | G06F 16/3329 |
| 2019/0198174 | A1 | 6/2019 | Abbaspour et al. | |
| 2020/0194121 | A1 | 6/2020 | Kupershmidt et al. | |
| 2020/0364366 | A1* | 11/2020 | Kundu | G06N 3/04 |
| 2021/0296002 | A1 | 9/2021 | Jia et al. | |
| 2022/0076101 | A1* | 3/2022 | Yang | G06F 18/22 |
| 2022/0147585 | A1 | 5/2022 | Sheshmani et al. | |
| 2022/0254513 | A1 | 8/2022 | Chen et al. | |
| 2022/0398233 | A1* | 12/2022 | Eloul | G06F 16/285 |
| 2023/0052865 | A1* | 2/2023 | Chen | G06N 3/08 |
| 2023/0074771 | A1* | 3/2023 | Nefedov | G06F 16/9024 |
| 2023/0208725 | A1* | 6/2023 | Tzoreff | G06N 5/01 709/226 |
| 2024/0045895 | A1* | 2/2024 | Akimoto | G06N 3/08 |
| 2024/0054339 | A1* | 2/2024 | Chen | G08G 1/0145 |

OTHER PUBLICATIONS

Bahdanau, Dzmitry et al. "Neural Machine Translation By Jointly Learning To Align and Translate," arXiv: 1409.0173v6 [cs.CL], Apr. 24, 2015, pp. 1-15, Published as a Conference Paper At ICLR 2015, available online: https://arxiv.org/pdf/1409.0473v6.pdf.

Choi, Youngduck et al. "Learning Low-Dimensional Representations Of Medical Concepts," Proceedings AMIA Joint Summits On Translational Science, vol. 2016, pp. 41-50, Jul. 20, 2016, PMCID: PMC5001761, PMID: 27570647, available online: https://www.ncbi.nlm.nih.gov/pmc/articles/PMC5001761/.

De Winter, Willem et al. "A Mechanism-Based Disease Progression Model For Comparison Of Long-Term E_Ects Of Pioglitazone, Metformin And Gliclazide On Disease Processes Underlying Type 2 Diabetes Mellitus," Journal of Pharmacokinetics and Pharmacodynamics, vol. 33, No. 3, Jun. 2006, pp. 313-343, DOI: 10.1007/s10928-006-9008-2.

Ito, Kaori et al. "Disease Progression Meta-Analysis Model In Alzheimer's Disease," Alzheimers Dementia, vol. 1, No. 1, Jan. 2010, pp. 39-53, (Epub: Jul. 9, 2009), PMID: 19592311, DOI: 10.1016/j.jalz.2009.05.665.

Jackson, Christopher H. et al. "Multistate Markov Models For Disease Progression With Classification Error," The Statistician, vol. 52, Part 2, pp. 193-209, Year: 2003), available online: http://www.leg.ufpr.br/~silvia/papers/mmm.pdf.

Li, Yang et al. "Knowledge Guided Diagnosis Prediction Via Graph Spatial-Temporal Network," In Proceedings of the 2020 SIAM International Conference on Data Mining (Year: 2020), pp. 19-27, Society for Industrial and Applied Mathematics, available online: https://epubs.siam.org/doi/pdf/10.1137/1.9781611976236.3.

Lipton, Zachary C. et al. "Learning To Diagnose With LSTM Recurrent Neural Networks," arXiv: 1511.03677v2 [cs.LG], Mar. 1, 2016, pp. 1-18, Published as a conference paper at ICLR 2016, available online: https://arxiv.org/pdf/1511.03677v6.pdf.

Liu, Jingshu et al. "Deep EHR: Chronic Disease Prediction Using Medical Notes," In Machine Learning for Healthcare Conference, Nov. 29, 2018, pp. 440-464, PMLR.

Liu, Yu-Ying et al. "Longitudinal Modeling Of Glaucoma Progression Using 2-Dimensional Continuous-Time Hidden Markov Model," In Medical Image Computing and Computer-Assisted Intervention, vol. 16, Part 2, pp. 444-451, (Year: 2013), Author Manuscript available in PMC Jun. 5, 2018.

Ma, Fenlong et al. "Dipole: Diagnosis Prediction In Healthcare Via Attention-Based Bidirectional Recurrent Neural Networks," In Proceedings of the 23rd ACM SIGKDD International Conference On Knowledge Discovery and Data Mining, Aug. 13, 2017 pp. 1903-1911, Halifax, NS, Canada.

Mould, D.R. "Models For Disease Progression: New Approaches and Uses," Clinical Pharmacology & Therapeutics, vol. 92, Issue 1, Quantitative Models, May 23, 2012, pp. 125-131, DOI: 10.1038/clpt.2012.53.

Ochoa, Juan G. Diaz et al. "Graph Neural Network Modelling As A Potentially Effective Method For Predicting and Analyzing Procedures Based On Patient Diagnoses," Artificial Intelligence in Medicine, Nov. 25, 2021, vol. 131:102359, pp. 1-17, available online: https://www.medrxiv.org/content/medrxiv/early/2021/12/02/2021.11.25.21266465.full.pdf.

Qiao, Zhi et al. "MNN: Multimodal Attentional Neural Networks For Diagnosis Prediction," Proceedings of the Twenty-Eighth International Joint Conference On Artificial Intelligence (IJCAI-19), pp. 5937-5943, (Year: 2019), available online: https://www.ijcai.org/Proceedings/2019/0823.pdf.

Ranganath, Rajesh et al. "The Survival Filter: Joint Survival Analysis with a Latent Time Series," In UAI, Jul. 12, 2015, pp. 742-751, available online: http://auai.org/uai2015/proceedings/papers/246.pdf.

Singer, Uriel et al. "Node Embedding over Temporal Graphs," Proceedings of the Twenty-Eighth International Joint Conference On Artificial Intelligence (IJCAI-19), pp. 4605-4612, Mar. 21, 2019, DOI: 10.24963/ijcai.2019/640.

Sukkar, Rafid et al. "Disease Progression Modeling Using Hidden Markov Models," 2012 Annual International Conference of the IEEE Engineering in Medicine and Biology Society, Aug. 28-Sep. 1, 2012, pp. 2845-2848, DOI: 10.1109/EMBC.2012.6346556, San Diego, CA, USA.

Tadano, Yara de Souza et al. "Unorganized Machines To Estimate The Number Of Hospital Admissions Due To Respiratory Diseases Caused By PM10 Concentration," Atmosphere, vol. 12, No. 1345, Oct. 14, 2021, DOI: 10.3390/atmos12101345.

Tangri, Navdeep et al. A Predictive Model For Progression of Chronic Kidney Disease To Kidney Failure, JAMA, vol. 305, No. 15, Apr. 20, 2011, pp. 1553-1559, DOI: 10.1001/jama.2011.451.

Wang, Xiang et al. "Unsupervised Learning Of Disease Progression Models," In Proceedings of the 20th ACM SIGKDD International Conference On Knowledge Discovery and Data Mining, Aug. 24-27, 2014, pp. 85-94, DOI: 10.1145/2623330.2623754, available online: https://people.csail.mit.edu/dsontag/papers/WanSonWan_kdd14.pdf.

Zhang, Tianran et al. "Diagnostic Prediction With Sequence-Of-Sets Representation Learning For Clinical Events," In Artificial Intelligence in Medicine: 18th International Conference On Artificial Intelligence In Medicine, AIME 2020, Minneapolis, MN, USA, Aug. 25-28, 2020, pp. 348-358, DOI: 10.1007/978-3-030-59137-3_31.

Zhou, Jiayu et al. "Modeling Disease Progression Via Fused Sparse Group Lasso," In Proceedings of the 18th ACM SIGKDD International Conference On Knowledge Discovery and Data Mining, Aug. 12, 2012, pp. 1095-1103, Author Manuscript available in PMC Oct. 9, 2014, DOI: 10.1145/2339530.2339702.

Choi, Edward et al. "Doctor AI: Predicting Clinical Events Via Recurrent Neural Networks," In Proceedings of Machine Learning for Healthcare Conference, JMLR W&C Trace vol. 56, Dec. 10, 2016, pp. 1-18 pages, available online: http://proceedings.mlr.press/v56/Choi16.pdf.

Colbaugh, Rich et al. "Learning To Identify Rare Disease Patients From Electronic Health Records," In American Medical Informatics Association (AMIA) Annual Symposium Proceedings, vol. 2018, pp. 340-347, Dec. 5, 2018, available online: https://www.ncbi.nlm.nih.gov/pmc/articles/PMC6371307/pdf/2976133.pdf.

Ehsani-Moghaddam, Behrouz et al. "Mucopolysaccharidosis Type II Detection By Naive Bayes Classifier: An Example of Patient Classification For A Rare Disease Using Electronic Medical Records From The Canadian Primary Care Sentinel Surveillance Network," PLoS One, vol. 13, No. 12:e0209018, pp. 1-17, Dec. 19, 2018, available online: https://journals.plos.org/plosone/article?id=10.1371/journal.pone.0209018.

Ghorbani, Mahsa et al. "RA-GCN: Graph Convolutional Network for Disease Prediction Problems with Imbalanced Data," arXiv preprint arXiv:2103.00221v3 [cs.LG], Nov. 7, 2021, pp. 1-18, available online: https://arxiv.org/pdf/2103.00221.pdf.

Goldstein, Ira et al. "Three Approaches to Automatic Assignment of ICD-9-CM Codes to Radiology Reports," AMIA Annual Symposium Proceedings Archive, Oct. 11, 2007, pp. 279-283. PMID:

(56) References Cited

OTHER PUBLICATIONS

18693842; PMCID: PMC2655861, available online: https://www.ncbi.nlm.nih.gov/pmc/articles/PMC2655861/.
Hochreiter, Sepp et al. "Long Short-Term Memory," Neural Computation, vol. 9, No. 8, pp. 1-32, Nov. 15, 1997.
Kavuluru, Ramakanth et al. "Unsupervised Extraction of Diagnosis Codes from EMRs Using Knowledge-Based and Extractive Text Summarization Techniques," Advanced Artificial Intelligence, vol. 7884, pp. 77-88, May 2013, DOI: 10.1007/978-3-642-38457-8_7, PMID: 28748227, PMCID: PMC5524149, available online: https://www.ncbi.nlm.nih.gov/pmc/articles/PMC5524149/pdf/nihms877790.pdf.
Kingma, Diederik P. et al. "Adam: A Method For Stochastic Optimization," arXiv preprint arXiv:1412.6980v8 [cs.LG], pp. 1-15, Jul. 23, 2015, available online: https://arxiv.org/pdf/1412.6980v8.pdf.
Li, Xuedong et al. "Improving Rare Disease Classification Using Imperfect Knowledge Graph," BMC Medical Informatics and Decision Making, vol. 19 (Suppl. 5):238, pp. 1-10, Jun. 10, 2019, available online: DOI: 10.1186/s12911-019-0938-1.
Mullenbach, James et al. "Explainable Prediction Of Medical Codes From Clinical Text," Proceedings of the 2018 Conference of the North American Chapter of the Association for Computational Linguistics: Human Language Technologies, vol. 1 (Long Papers), pp. 1101-1111, Jun. 2018, New Orleans, Louisiana. Association for Computational Linguistics, DOI: 10.18653/v1/N18-1100.
Su, Chenhao et al. "Gate: Graph-Attention Augmented Temporal Neural Network for Medication Recommendation," IEEE Access, vol. 8, pp. 125447-125458, Jul. 7, 2020, DOI: 10.1109/ACCESS.2020.3007835.
Sun, Zhenchao et al. "Disease Prediction Via Graph Neural Networks," IEEE Journal of biomedical and Health Informatics. vol. 25, No. 3, pp. 818-826, Mar. 2021.
Tai, Kai Shent et al. "Improved Semantic Representations From Tree-Structured Long Short-Term Memory Networks," In Proceedings of the 53rd Annual Meeting of the Association for Computational Linguistics and the 7th International Joint Conference on Natural Language Processing, vol. 1: Long Papers, pp. 1556-1566, Beijing, China. Association for Computational Linguistics, DOI: 10.3115/v1/P15-1150.
Velickovic, Petar et al. "Graph Attention Networks," arXiv preprint arXiv: 1710.10903v3 [stat.ML], Feb. 4, 2018, pp. 1-12, available online: https://personal.utdallas.edu/~fxc190007/courses/20S-7301/GAT-questions.pdf.
Wang, Qifan. "Health Information Network Representation Learning," Thesis submitted to McGill University, Aug. 27, 2020, (82 pages), Canada.
Wang, Shanshan et al. "Few-Shot Electronic Health Record Coding Through Graph Contrastive Learning," arXiv Preprint arXiv:2106.15467v1 [cs.AI], Jun. 29, 2021, pp. 1-14, available online: https://arxiv.org/pdf/2106.15467.pdf.
Xie, Pengtao et al. "A Neural Architecture for Automated ICD Coding," Proceedings of the 56th Annual Meeting of the Association for Computational Linguistics, vol. 1: Long Papers, Jul. 2018, pp. 1066-1076, Melbourne, Australia. Association for Computational Linguistics, DOI: 10.18653/v1/P18-1098.
Zhu, Weicheng et al. "Variationally Regularized Graph-Based Representation Learning For Electronic Health Records," In Proceedings of the Conference on Health, Inference, and Learning (ACM CHIL '21), pp. 1-13, Apr. 8, 2021, Virtual Event, USA, ACM, New York, NY, DOI: 10.1145/3450439.3451855.
Bowman, Nicholas, et al., "Temporal Link Prediction on the WikiLinkGraphs Dataset", Stanford Student Course (CS224W) Project, Fall 2018, available on the Internet at https://snap.stanford.edu/class/cs224w-2019/project/26425112.pdf, 11 pages.
Geng, Zhiqiang, et al., "Semantic relation extraction using sequential and tree-structured LSTM with attention", Information Sciences, Sep. 10, 2019, pp. 183-192, vol. 509, Elsevier, Inc., US.
Notice of Allowance and Fees Due (PTOL-85) Mailed on Jun. 24, 2026 for U.S. Appl. No. 18/153,047, 10 page(s).
Xia, Feng, et al., "Graph Learning: A Survey", IEEE Transactions on Artificial Intelligence, Apr. 2021, pp. 109-127, IEEE, US.

* cited by examiner

ATTENTION-BASED MACHINE LEARNING TECHNIQUES USING TEMPORAL SEQUENCE DATA AND DYNAMIC CO-OCCURRENCE GRAPH DATA OBJECTS

BACKGROUND

Various embodiments of the present disclosure address technical challenges related to performing predictive data analysis and provide solutions to address the efficiency and reliability shortcomings of existing predictive data analysis solutions.

BRIEF SUMMARY

In general, various embodiments of the present disclosure provide methods, apparatus, systems, computing devices, computing entities, and/or the like for generating a representative embeddings for a plurality of temporal sequences by using a graph attention augmented temporal network based at least in part on dynamic co-occurrence graphs for preceding temporal sequences and initial embeddings, where the dynamic co-occurrence graphs are projections of a global guidance co-occurrence graph on features of the preceding temporal sequences, and the initial embeddings are generated by processing a latent representation of corresponding features that is generated by a sequential long short term memory model as well as a feature tree using a tree-based long short term memory model.

In accordance with one aspect, a method is provided. In one embodiment, the method comprises: receiving, by a computing device, one or more input data objects, each input data object comprising a temporal sequence in a plurality of temporal sequences and comprising a related feature subset of a plurality of features associated with the temporal sequence; generating, by the computing device, a global guidance correlation graph data object, wherein: (i) each node of the global guidance correlation graph data object corresponds to a feature in the plurality of features, and (ii) each edge of the global guidance correlation graph data object corresponds to a feature pair and describes a co-occurrence probability for the feature pair; for each temporal sequence, generating, by the computing device, one or more dynamic co-occurrence graph data object based at least in part on the global guidance correlation graph, wherein each dynamic co-occurrence graph data object for a particular temporal sequence describes a projection of the global guidance correlation graph data object on the input data object for the temporal sequence; generating, by the computing device, using the machine learning model, and based at least in part on the plurality of temporal sequences and each dynamic co-occurrence graph data object, one or more predicted classification labels, wherein: the machine learning model comprises a graph-attention augmented temporal neural network machine learning model comprising a plurality of embedding layers, training the machine learning model comprises, for each combination of a given temporal sequence t of T number of temporal sequences in the plurality of temporal sequences, a given non-initial embedding layer l of the one or more embedding layers, and a given feature i of the plurality of features, generating a historical node representation based at least in part on: (i) a prior-layer historical node representation for the given temporal sequence t and the given feature i as generated by a preceding embedding layer l−1, and (ii) neighbor nodes for a target node associated with the given feature i in the dynamic co-occurrence graph corresponding to the given temporal sequence t, an initial embedding layer is configured to, for an initial temporal sequence, generate historical node representations for the plurality of features using a tree-of-sequences based at least in part on initial embeddings that are generated using a sequential long short-term memory machine learning model; and performing one or more prediction-based actions based at least in part on the one or more predictive classification labels.

In accordance with another aspect, an apparatus comprising at least one processor and at least one memory including computer program code is provided. In one embodiment, the at least one memory and the computer program code may be configured to, with the processor, cause the apparatus to: receive one or more input data objects, each input data object comprising a temporal sequence in a plurality of temporal sequences and comprising a related feature subset of a plurality of features associated with the temporal sequence; generate a global guidance correlation graph data object, wherein: (i) each node of the global guidance correlation graph data object corresponds to a feature in the plurality of features, and (ii) each edge of the global guidance correlation graph data object corresponds to a feature pair and describes a co-occurrence probability for the feature pair; for each temporal sequence, generate one or more dynamic co-occurrence graph data object based at least in part on the global guidance correlation graph, wherein each dynamic co-occurrence graph data object for a particular temporal sequence describes a projection of the global guidance correlation graph data object on the input data object for the temporal sequence; generate, using the machine learning model, and based at least in part on the plurality of temporal sequences and each dynamic co-occurrence graph data object, one or more predicted classification labels, wherein: the machine learning model comprises a graph-attention augmented temporal neural network machine learning model comprising a plurality of embedding layers, training the machine learning model comprises, for each combination of a given temporal sequence t of T number of temporal sequences in the plurality of temporal sequences, a given non-initial embedding layer l of the one or more embedding layers, and a given feature i of the plurality of features, generating a historical node representation based at least in part on: (i) a prior-layer historical node representation for the given temporal sequence t and the given feature i as generated by a preceding embedding layer l−1, and (ii) neighbor nodes for a target node associated with the given feature i in the dynamic co-occurrence graph corresponding to the given temporal sequence t, an initial embedding layer is configured to, for an initial temporal sequence, generate historical node representations for the plurality of features using a tree-of-sequences based at least in part on initial embeddings that are generated using a sequential long short-term memory machine learning model; and perform one or more prediction-based actions based at least in part on the one or more predictive classification labels.

In accordance with yet another aspect, a computer program product is provided. The computer program product may comprise at least one computer-readable storage medium having computer-readable program code portions stored therein, the computer-readable program code portions comprising executable portions configured to: receive one or more input data objects, each input data object comprising a temporal sequence in a plurality of temporal sequences and comprising a related feature subset of a plurality of features associated with the temporal sequence; generate a global guidance correlation graph data object, wherein: (i) each node of the global guidance correlation graph data object corresponds to a feature in the plurality of features, and (ii) each edge of the global guidance correlation graph data object corresponds to a feature pair and describes a co-occurrence probability for the feature pair; for each temporal sequence, generate one or more dynamic co-occurrence graph data object based at least in part on the global guidance correlation graph, wherein each dynamic co-occurrence graph data object for a particular temporal sequence describes a projection of the global guidance correlation graph data object on the input data object for the temporal sequence; generate, using the machine learning model, and based at least in part on the plurality of temporal sequences and each dynamic co-occurrence graph data object, one or more predicted classification labels, wherein: the machine learning model comprises a graph-attention augmented temporal neural network machine learning model comprising a plurality of embedding layers, training the machine learning model comprises, for each combination of a given temporal sequence t of T number of temporal sequences in the plurality of temporal sequences, a given non-initial embedding layer l of the one or more embedding layers, and a given feature i of the plurality of features, generating a historical node representation based at least in part on: (i) a prior-layer historical node representation for the given temporal sequence t and the given feature i as generated by a preceding embedding layer l−1, and (ii) neighbor nodes for a target node associated with the given feature i in the dynamic co-occurrence graph corresponding to the given temporal sequence t, an initial embedding layer is configured to, for an initial temporal sequence, generate historical node representations for the plurality of features using a tree-of-sequences based at least in part on initial embeddings that are generated using a sequential long short-term memory machine learning model; and perform one or more prediction-based actions based at least in part on the one or more predictive classification labels.

BRIEF DESCRIPTION OF THE DRAWINGS

Figure 1:
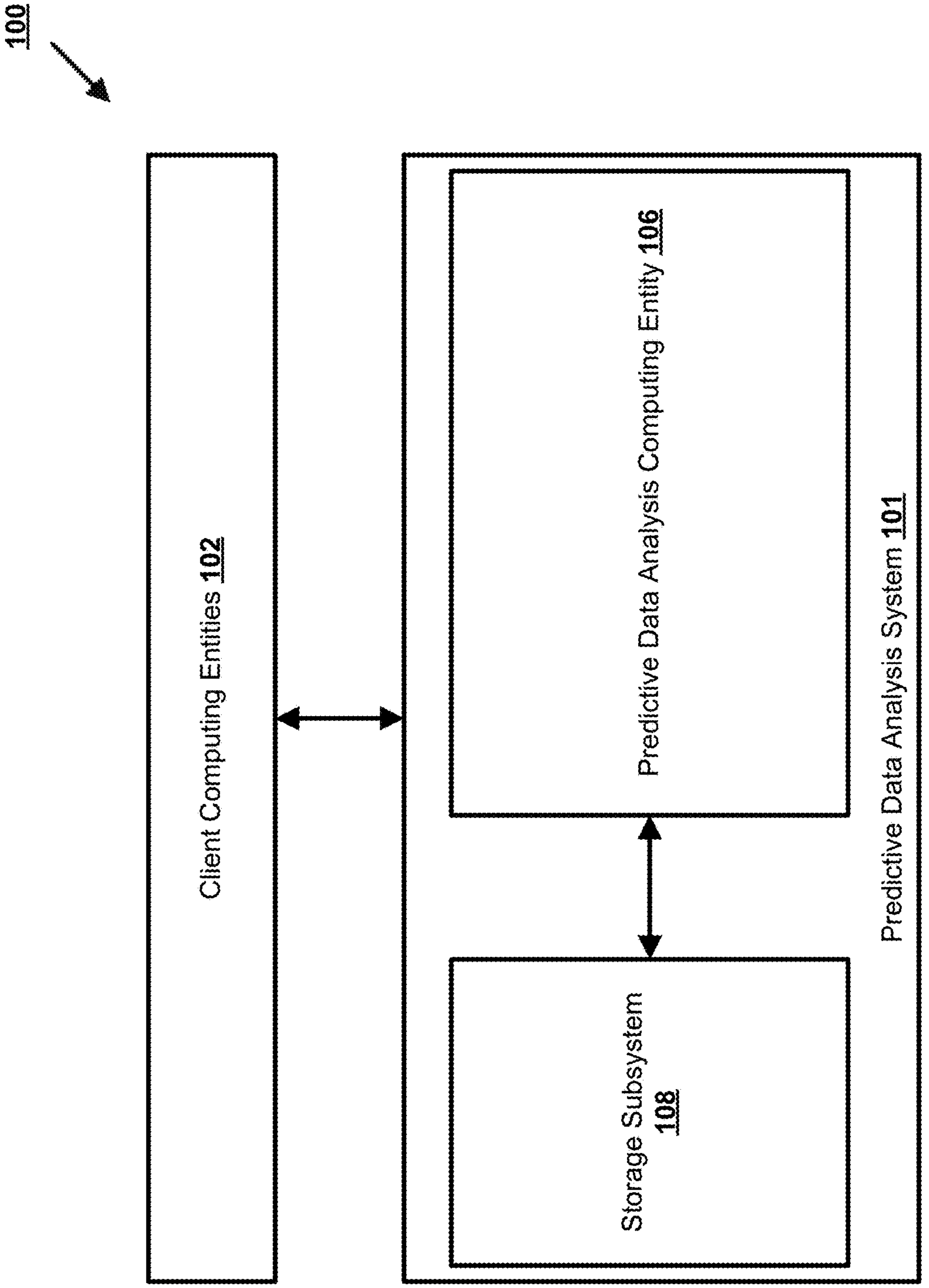

Having thus described the disclosure in general terms, reference will now be made to the accompanying drawings, which are not necessarily drawn to scale, and wherein:

FIG. 1 provides an exemplary overview of an architecture that can be used to practice embodiments of the present disclosure.

Figure 2:
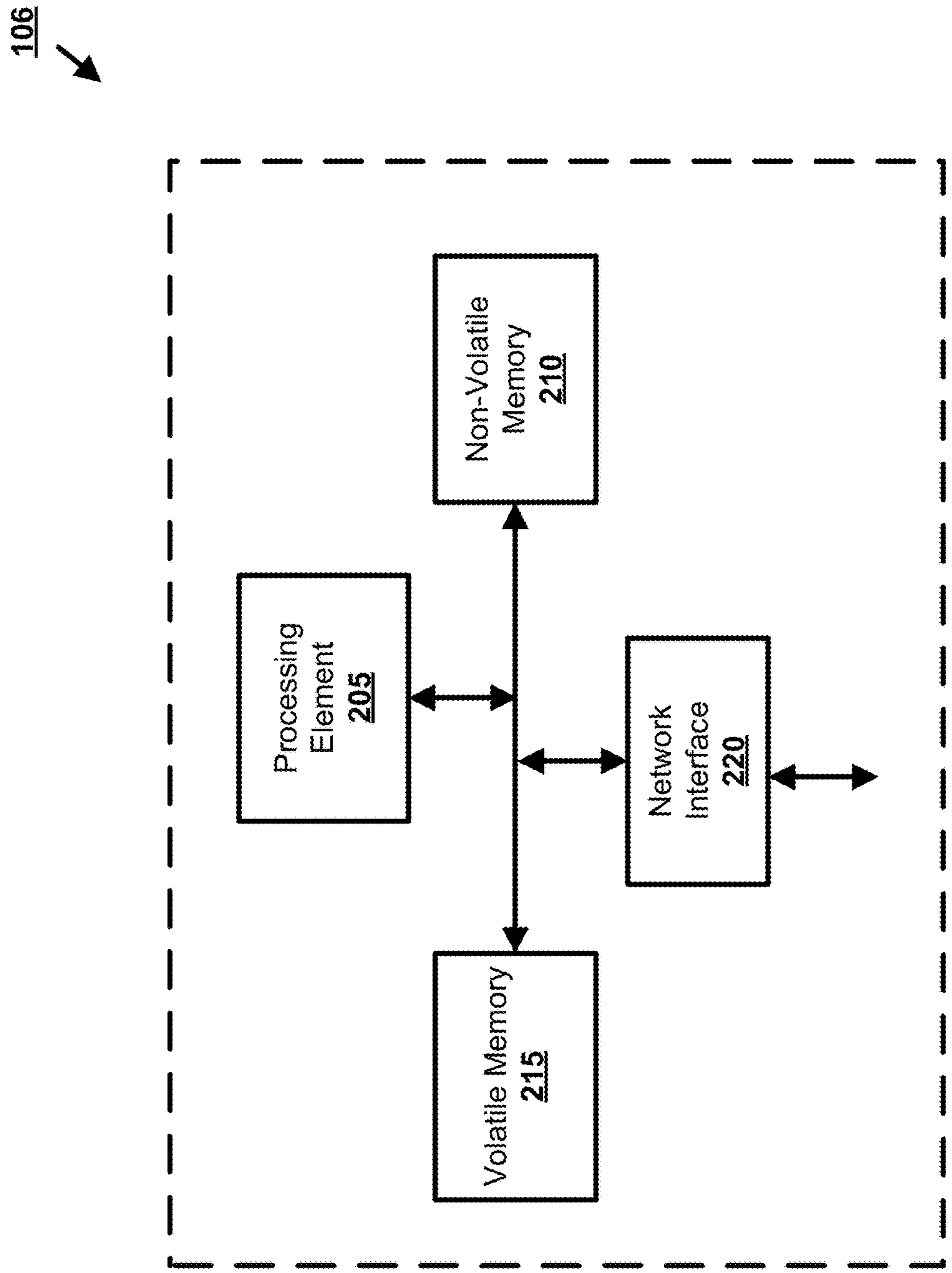

FIG. 2 provides an example predictive data analysis computing entity in accordance with some embodiments discussed herein.

Figure 3:
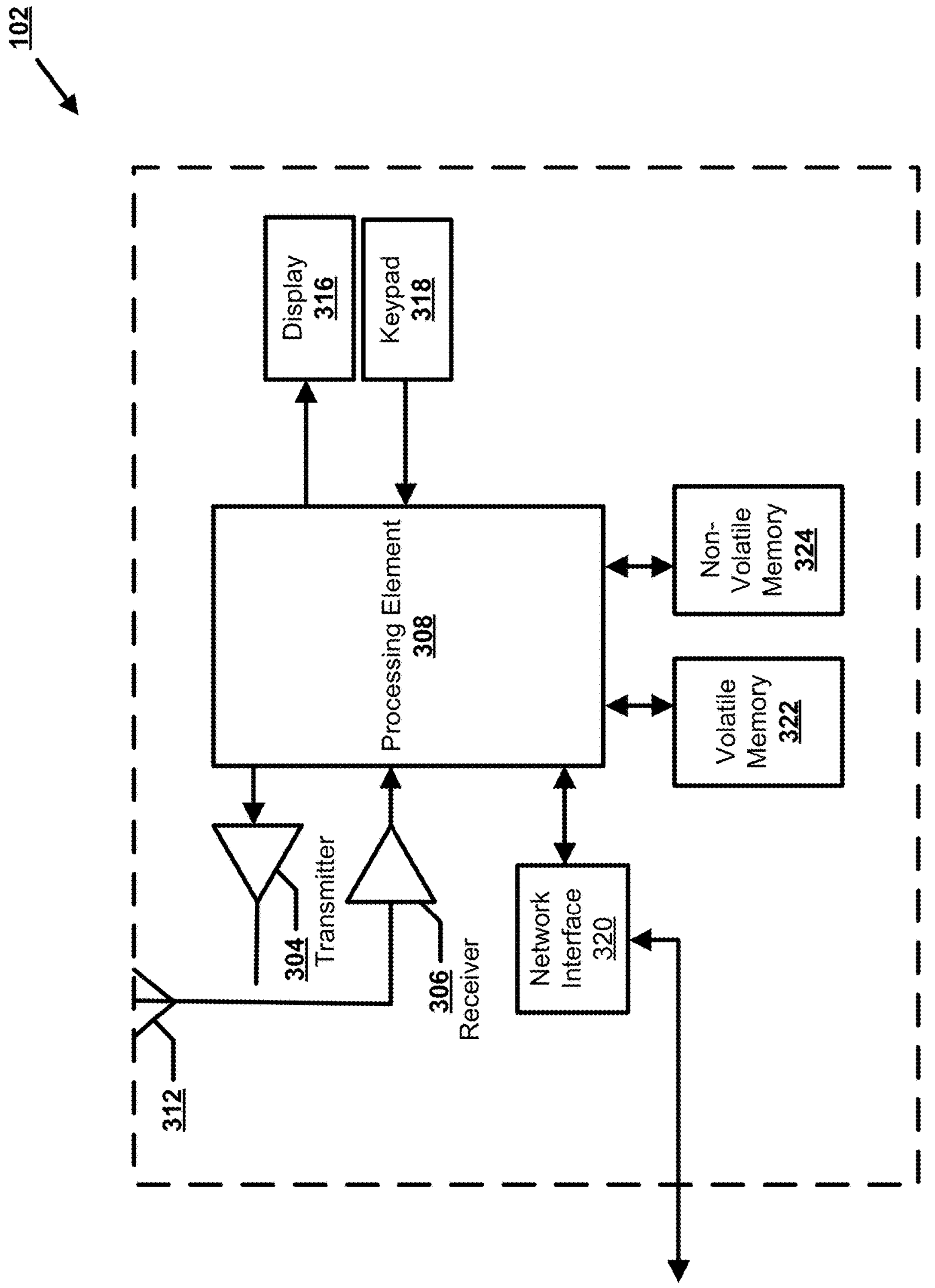

FIG. 3 provides an example client computing entity in accordance with some embodiments discussed herein.

Figure 4:
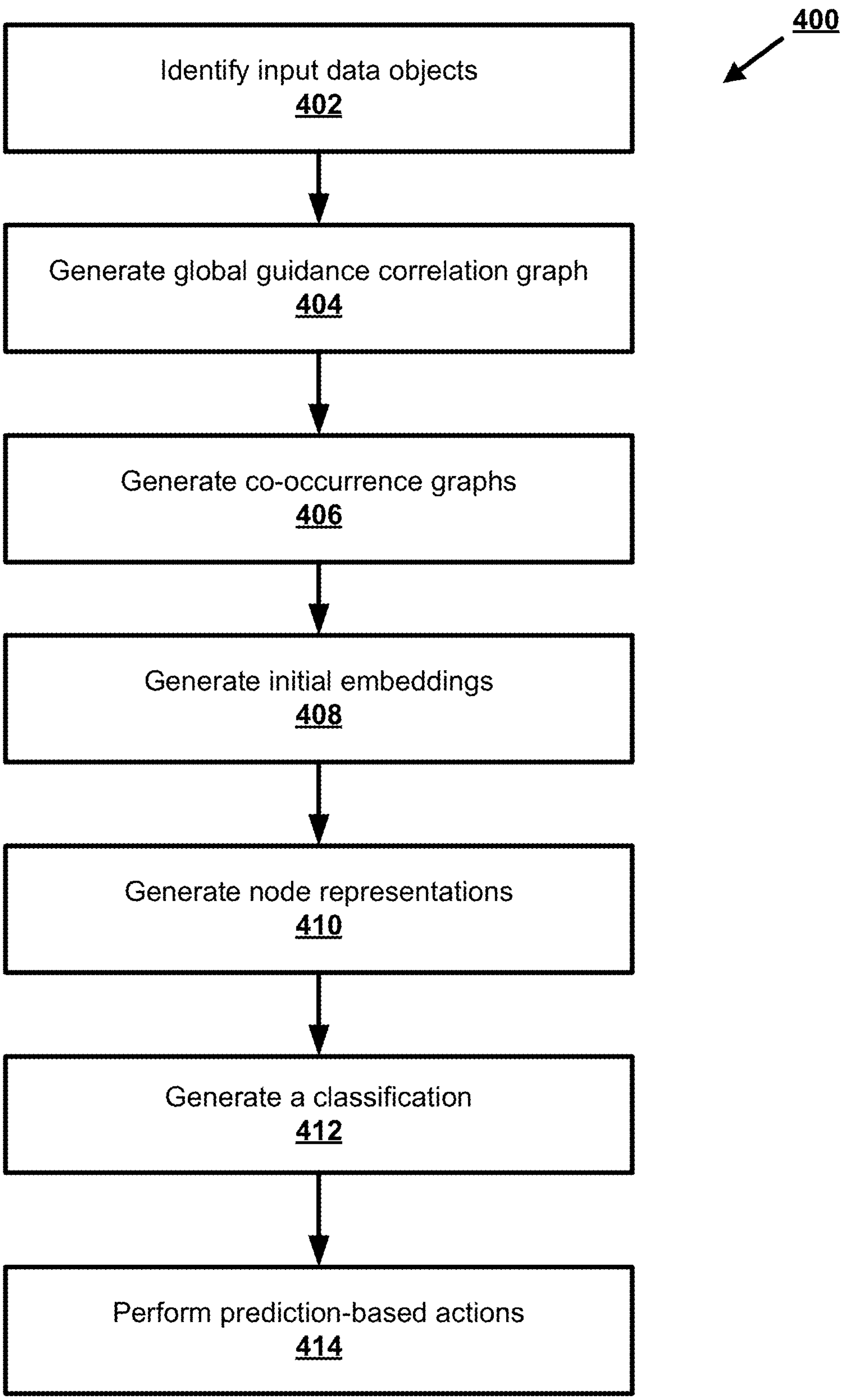

FIG. 4 presents a flowchart diagram of an example process for performing classification operations on input data objects comprising sets of temporal sequences in accordance with some embodiments discussed herein.

Figure 5:
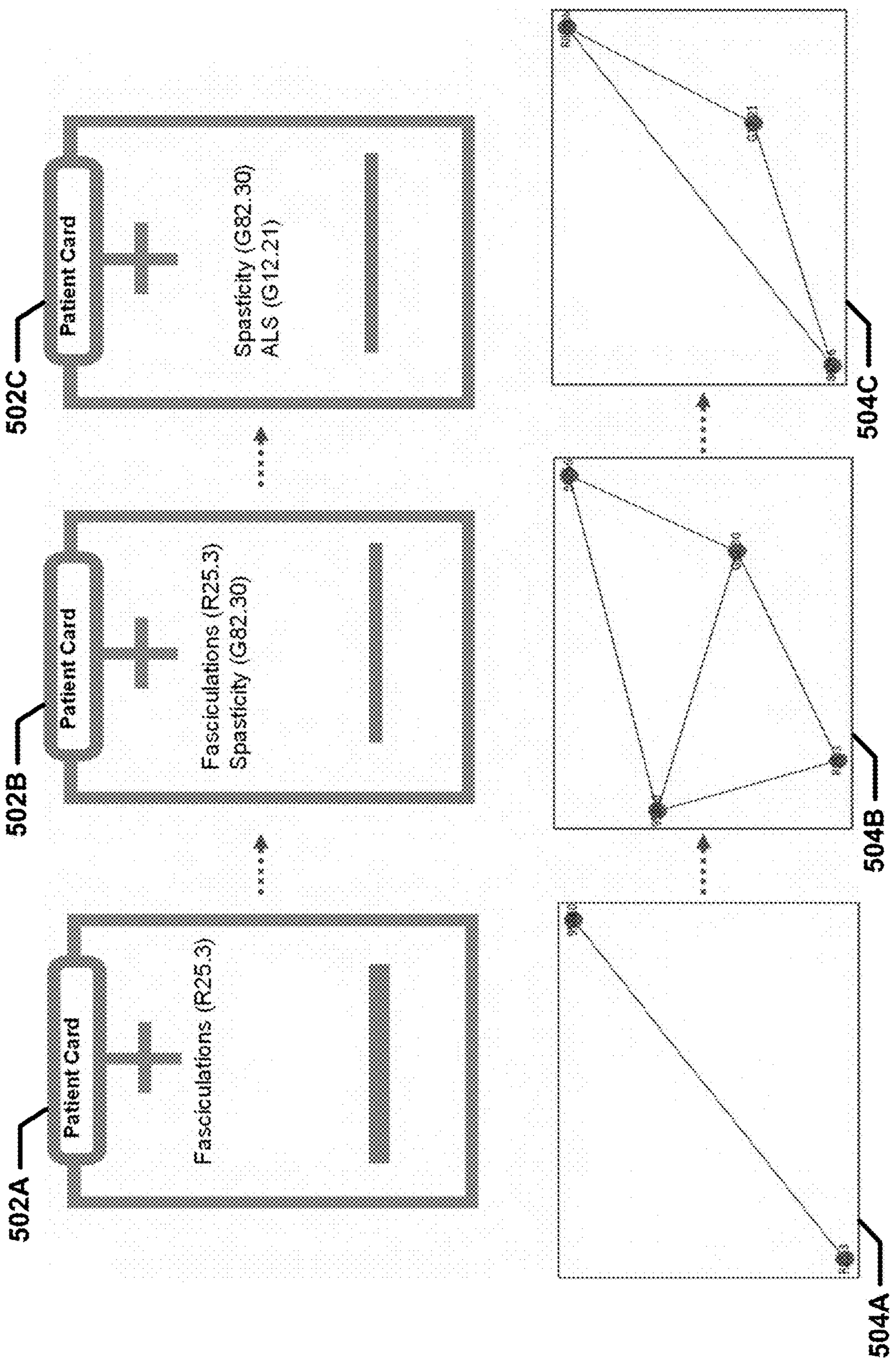

FIG. 5 presents an operational example of dynamic co-occurrence graphs in accordance with some embodiments discussed herein.

Figure 6:
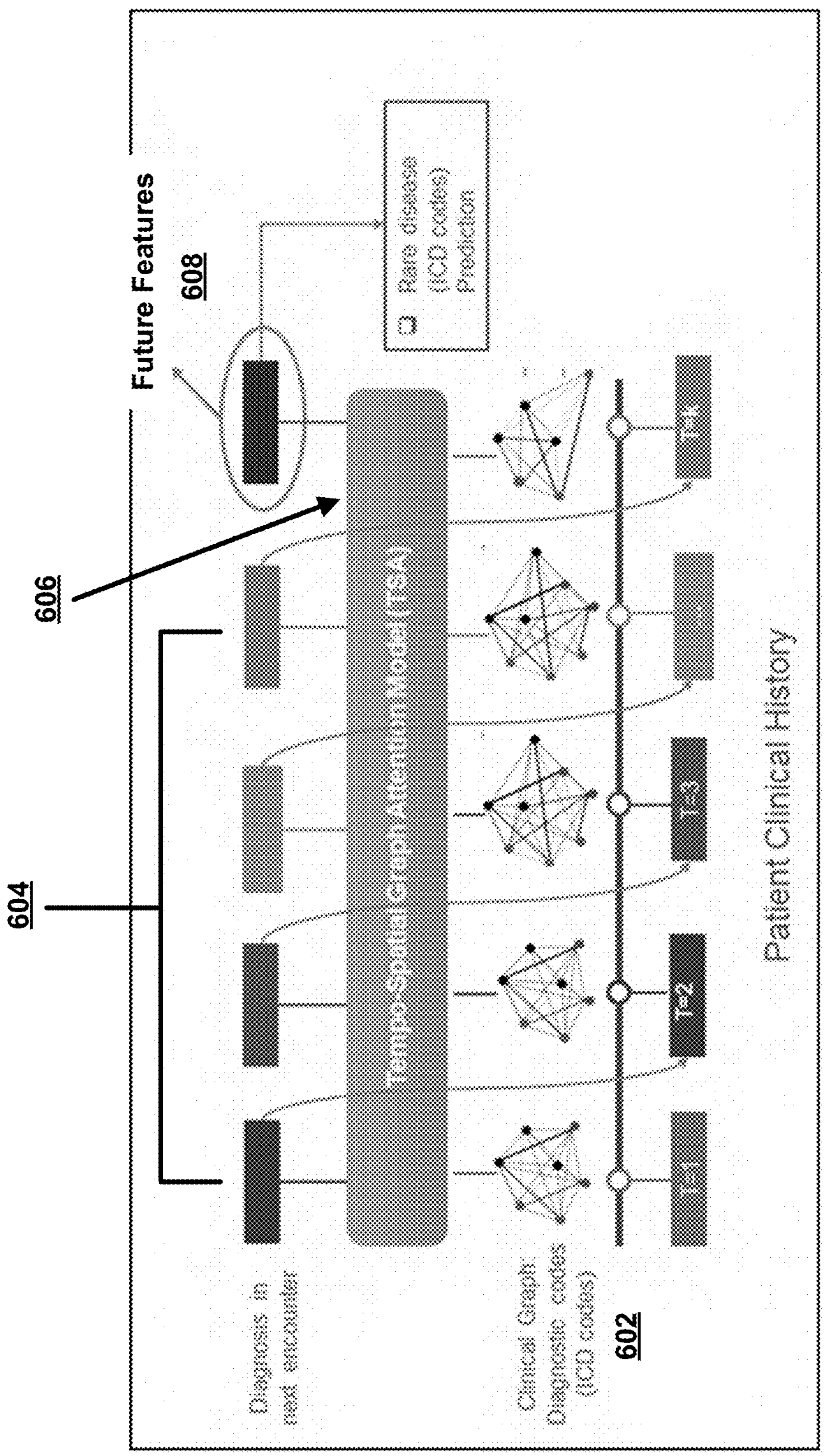

FIG. 6 presents an operational example of building historical node representations in accordance with some embodiments discussed herein.

Figure 7:
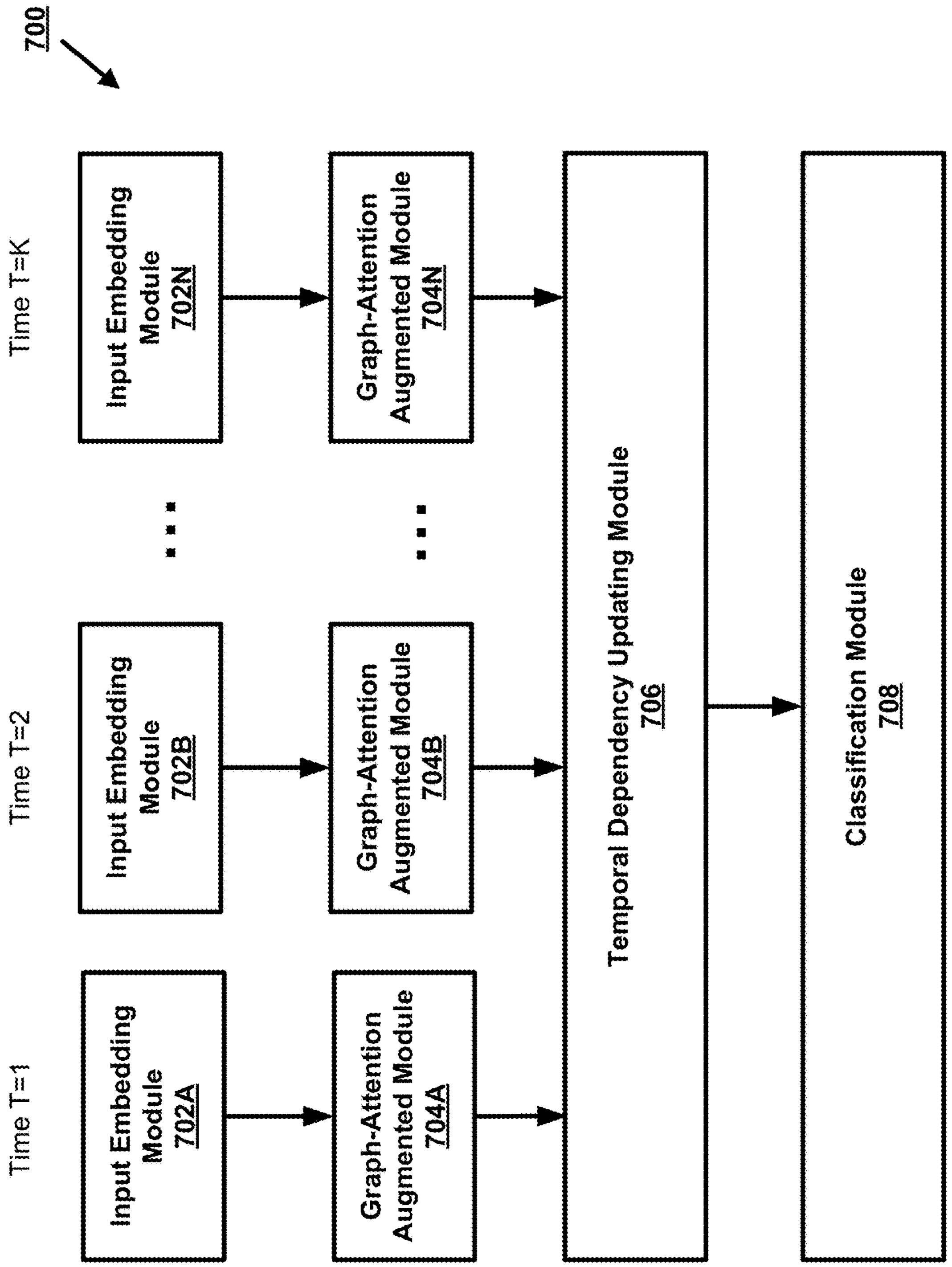

FIG. 7 presents a machine learning framework in accordance with some embodiments discussed herein.

DETAILED DESCRIPTION

Various embodiments of the present disclosure now will be described more fully hereinafter with reference to the accompanying drawings, in which some, but not all, embodiments of the disclosure are shown. Indeed, the disclosure may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present disclosure are described with reference to predictive data analysis, one of ordinary skill in the art will recognize that the disclosed concepts can be used to perform other types of data analysis.

I. Overview and Technical Improvements

Various embodiments of the present disclosure make important technical contributions to improving predictive accuracy of machine learning models, which in turn improves training speed and training efficiency of machine learning models. It is well-understood in the relevant art that there is typically a tradeoff between predictive accuracy and training speed, such that it is trivial to improve training speed by reducing predictive accuracy, and thus the real challenge is to improve training speed without sacrificing predictive accuracy through innovative model architectures, see, e.g., Sun et al., *Feature-Frequency—Adaptive On-line Training for Fast and Accurate Natural Language Processing* in 40(3) Computational Linguistic 563 at Abst. ("Typically, we need to make a tradeoff between speed and accuracy. It is trivial to improve the training speed via sacrificing accuracy or to improve the accuracy via sacrificing speed. Nevertheless, it is nontrivial to improve the training speed and the accuracy at the same time"). Accordingly, the techniques described herein improve predictive accuracy without harming training speed, such as various techniques described herein, enable improving training speed given a constant predictive accuracy. In doing so, the techniques described herein improve accuracy, efficiency, and speed of machine learning models, thus reducing the number of computational operations needed and/or the amount of training data entries needed to train machine learning models. Accordingly, the techniques described herein improve at least one of the computational efficiency, storage-wise efficiency, and speed of training machine learning models.

For example, various embodiments of the present disclosure improve accuracy of machine learning models by pre-training models with features (e.g., clinical events) based at least in part on textual content as well as hierarchical structure among the features. As described herein, a collection of information, such as an electronic health record ("EHR"), may comprise a large number of features associated with a temporal structure. Existing methods for performing a prediction on a collection of information may include building a prediction model based at least in part on the features and making a prediction. However, existing methods are limited in their abilities in dealing with complex structural correlations and temporal dependencies of features in a temporal sequence (e.g., admission), which may impact classification predictions as well as temporal prediction of classification labels.

However, in accordance with various embodiments of the present disclosure, a temporal-spatial approach may be used to capture temporal feature set (e.g., health) progression as well as relationships among different features over a period. This technique will lead to higher accuracy of performing predictions on input comprising a temporal sequence. In doing so, the techniques described herein improving efficiency and speed of training natural language processing machine learning models, thus reducing the number of computational operations needed and/or the amount of training data entries needed to train machine learning models. Accordingly, the techniques described herein improve at least one of the computational efficiency, storage-wise efficiency, and speed of training machine learning models.

An exemplary application of various embodiments of the present disclosure relates to generating predictions for a given temporal sequence based at least in part on features from a set of temporal sequences. In some embodiments, an attentional encoder decoder model may be trained on a collection of information comprising a set of temporal sequences, where weights from the attentional encoder decoder model are transferred to a graph-attention augmented temporal neural network model which results in a better parameter initialization of the graph attention model. A key benefit of various embodiments of the present invention is the improved prediction outcome based at least in part on textual content as well as any hierarchical structure among text within an EHR. This improved accuracy of prediction also enables improved accuracy in further text processing tasks, such as coding quality and diagnosis. In some embodiments, the following operations are performed: generating a global guidance graph where each node is a diagnostic event; generating a dynamic co-occurrence graph for each temporal sequence weighted by co-occurrences of events; initializing embeddings using pretrained models and using temporal sequence level representation to learn temporal feature set progression using a graph attention augmented temporal neural network; and generating a prediction for a future temporal sequence.

In some embodiments, recommendation of a current admission may be generated by considering a patient's historical records and correlations among clinical events from every admission in the patient's historical records. Accordingly, various embodiments of the present disclosure deal with complex structural correlations and temporal dependencies of clinical events in EHRs, which results in improved recommendation quality and temporal prediction ability in the context of providing healthcare.

II. Definitions

The term "temporal sequence" may refer to a data construct that describes an input data object comprising an instance $$x_t^n = \{d_t\}$$

at a given time t, where n corresponds to a given entity and $d_t$ is representative of one or more features that describe the instance $$x_t^n.$$

A temporal sequence may comprise images, text files, audio/video files, and application files that may be used to, for example, train a machine learning model. For example, the instance may represent a patient admission on a given date and the given entity may represent a patient. Features within a temporal sequence may be internally related and include correlations of various degrees that may be interpreted with various meanings.

The term "set of temporal sequences" may refer to a data construct that describes a plurality of temporal sequences $$E_{1:T-1}^n = \{x_1^n, x_2^n, \ldots, x_{T-1}^n\}$$

of a given entity n for T number of time instances (e.g., dates). In some embodiments, the plurality of temporal sequences may be an ordered set of temporal sequences. As an example, the set of temporal sequences may comprise a patient's EHRs comprising a history of admissions where each of the plurality of temporal sequences may represent an admission within a time series. As such, a set of temporal sequences may be representative of a patient's condition over multiple admissions, procedures, and medications.

The term "feature" may refer to a data construct that describes an attribute or characteristic associated with an input data object, such as a temporal sequence, that may be used for analysis and training of a machine learning model. As an example, features of an input data object may comprise clinical events including diagnoses, associated symptoms, or medical codes, e.g., International Statistical Classification of Diseases and Related Health Problems (ICD) codes, Current Procedural Terminology (CPT) codes, prescription (RX) codes.

The term "initial embedding" may refer to a data construct that describes an initial representation of features from input data objects, where a feature matrix may be generated by processing the input data objects using an attentional encoder decoder machine learning model. For example, the initial embedding may comprise a translation of features from a temporal sequence to a feature matrix comprising a tree hierarchy using an input embedding module of the attentional encoder decoder machine learning model.

The term "attentional encoder decoder machine learning model" may refer to a data construct that describes parameters, hyperparameters, and/or defined operations of a machine learning model, where the machine learning model is configured to translate features into a feature matrix by processing input data objects. As described above, the attentional encoder decoder machine learning model may comprise at least an input embedding module that translates features from a temporal sequence to a feature matrix. In some embodiments, the feature matrix may be created by using a tree-of-sequences LSTM network. According to various embodiments of the present disclosure, the input embedding module may include a description encoder that generates a latent representation vector for a description corresponding to a feature. In some embodiments, each feature may be associated with a description that describes the semantics of the features. For example, a feature such as a diagnostic code may be associated with a short text description that describes the semantics of the diagnostic code. Other examples of such a description may include metadata or captioning. The description encoder may use a sequential long short-term memory ("LSTM") network to encode descriptions. The input embedding module may further include a feature encoder that creates a tree-of-sequences LSTM network to capture hierarchal relationships among the features. Each node of the tree-of-sequences LSTM network may comprise an input vector based at least in part on the latent representation generated by the sequential LSTM.

The term "LSTM network" may refer to a data construct that describes a recurrent neural network that stores a representation of features from sequences of input data objects, such as a set of temporal sequences, where long- and short-term information dependencies are preserved.

The term "sequential LSTM network" may refer to a data construct that describes a LSTM network that learns a latent representation of features (which may reflect certain semantic information) and models a sequential structure among the features.

The term "tree-of-sequences LSTM network" may refer to a data construct that describes a hierarchy of sequential LSTM networks. As described above, the tree-of-sequences LSTM network comprises features that are encoded by a sequential LSTM and applying a tree structure to the sequential LSTM to capture hierarchical relationships among the features. Each node of the tree-of-sequences LSTM network may comprise a vector including a latent representation based at least in part on the encoding by the sequential LSTM.

The term "global guidance correlation graph" may refer to a data construct that describes a graph including nodes that are representative of a universe of features appearing in a data set (e.g., of input data objects). For example, the nodes of a global guidance correlation graph may include all features in a dataset comprising a plurality of sets of temporal sequences associated with a plurality of entities. The global guidance correlation graph may further include edges that are based at least in part on co-occurrence probability between the universe of features. As an example, edges of a global guidance correlation graph may include weights that may be calculated based at least in part on total number of temporal sequences that a feature pair have co-occurred, total number of temporal sequences that features of the pair have appeared at least once, and total number of temporal sequences.

The term "dynamic co-occurrence graphs" may refer to a data construct that describes a plurality of semantic graphs including features associated with a plurality of temporal sequences over time. A dynamic co-occurrence graph may be constructed based at least in part on global correlations from a global guidance correlation graph. In some embodiments, dynamic co-occurrence graphs may comprise a sequence of adjacency matrices where each adjacency matrix in the sequence of adjacency matrices comprises a connected graph including nodes that represent features of a given temporal sequence of a set of temporal sequences associated with a given entity. The adjacency matrices may further include edges and edge weights based at least in part on a global guidance correlation graph.

The term "co-occurrence probability" may refer to a data construct that describes a measurement of relationship between two variables. In some embodiments, the relationship may comprise a semantic proximity of the two variables. For example, co-occurrence frequency may comprise an above-chance frequency of features coinciding or existing within a body of data.

The term "graph-attention augmented temporal neural network" may refer to a data construct that describes a two-layer graph-attention neural network for embedding historical node representations. In some embodiments, the graph-attention augmented temporal neural network model may update an initial embedding based at least in part on a dynamic co-occurrence graph. The graph-attention augmented temporal neural network may construct encoded feature vectors that contain information of other co-occurrence features of a same temporal sequence with different degrees of correlation to obtain more comprehensive representation. As an example, at each embedding layer, the graph-attention augmented temporal neural network can embed a set of historical node representations by recursively aggregating information from node neighbors based at least in part on the dynamic co-occurrence graphs.

The term "classification label" may refer to a data construct that describes descriptions, tags, or identifiers that classify or emphasize features present in a body of data.

The term "predictive classification label" may refer to a data construct that describes a prediction output of a machine learning model, such as a graph-attention augmented temporal neural network model. The prediction output may comprise a classification output including one or more classification labels based at least in part on a given input data object. As an example, in some embodiments, the classification labels may comprise medical codes, e.g., ICD codes, CPT codes, and RX codes that are generated as classification output for prediction on a set of temporal sequences. According to various embodiments of the present disclosure, a predictive classification label may comprise a diagnostic code for a rare disease $y_t=\{0,1\}^{L+1}$, where L is the number of rare diseases considered, and all other diseases are represented as a single binary vector.

III. Computer Program Products, Methods, and Computing Entities

Embodiments of the present disclosure may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatus, systems, computing devices, computing entities, and/or the like. As such, embodiments of the present disclosure may take the form of an apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises combination of computer program products and hardware performing certain steps or operations. Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. Exemplary System Architecture

FIG. 1 is a schematic diagram of an example architecture 100 for performing predictive data analysis. The architecture 100 includes a predictive data analysis system 101 configured to receive predictive data analysis requests from client computing entities 102, process the predictive data analysis requests to generate predictions, provide the generated predictions to the client computing entities 102, and automatically perform prediction-based actions based at least in part on the generated predictions.

An example of a prediction-based action that can be performed using the predictive data analysis system 101 is a request for generating a diagnosis code for one or more rare diseases based at least in part on an EHR of a patient and displaying the diagnosis code on a user interface. For example, in accordance with various embodiments of the present invention, a graph-attention augmented temporal neural network model may be used to generate predictions on a set of temporal sequences based at least in part on temporal feature set progression as well as relationships among different features over a period. This technique will lead to higher accuracy of performing predictions on input comprising a temporal sequence. In doing so, the techniques described herein improving efficiency and speed of training natural language processing machine learning models, thus reducing the number of computational operations needed and/or the amount of training data entries needed to train machine learning models. Accordingly, the techniques described herein improve at least one of the computational efficiency, storage-wise efficiency, and speed of training machine learning models.

In some embodiments, predictive data analysis system 101 may communicate with at least one of the client computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The predictive data analysis system 101 may include a predictive data analysis computing entity 106 and a storage subsystem 108. The predictive data analysis computing entity 106 may be configured to receive predictive data analysis requests from one or more client computing entities 102, process the predictive data analysis requests to generate predictions corresponding to the predictive data analysis requests, provide the generated predictions to the client computing entities 102, and automatically perform prediction-based actions based at least in part on the generated predictions.

The storage subsystem 108 may be configured to store input data used by the predictive data analysis computing entity 106 to perform predictive data analysis as well as model definition data used by the predictive data analysis computing entity 106 to perform various predictive data analysis tasks. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

A. Exemplary Predictive Data Analysis Computing Entity

FIG. 2 provides a schematic of a predictive data analysis computing entity 106 according to one embodiment of the present disclosure. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may include, or be in communication with, one or more processing elements 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present disclosure when configured accordingly.

In one embodiment, the predictive data analysis computing entity 106 may further include, or be in communication with, non-volatile media (also referred to as non-volatile storage, memory, memory storage, memory circuitry and/or similar terms used herein interchangeably). In one embodiment, the non-volatile storage or memory may include one or more non-volatile storage or memory media 210, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the predictive data analysis computing entity 106 may further include, or be in communication with, volatile media (also referred to as volatile storage, memory, memory storage, memory circuitry and/or similar terms used herein interchangeably). In one embodiment, the volatile storage or memory may also include one or more volatile storage or memory media 215, including, but not limited to, RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include, or be in communication with, one or more input elements, such as a keyboard input, a mouse input, a touch screen/display input, motion input, movement input, audio input, pointing device input, joystick input, keypad input, and/or the like. The predictive data analysis computing entity 106 may also include, or be in communication with, one or more output elements (not shown), such as audio output, video output, screen/display output, motion output, movement output, and/or the like.

B. Exemplary Client Computing Entity

FIG. 3 provides an illustrative schematic representative of a client computing entity 102 that can be used in conjunction with embodiments of the present disclosure. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Client computing entities 102 can be operated by various parties. As shown in FIG. 3, the client computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the client computing entity 102 may be capable of operating with one or more air interface standards, communication protocols, modulation types, and access types. More particularly, the client computing entity 102 may operate in accordance with any of a number of wireless communication standards and protocols, such as those described above with regard to the predictive data analysis computing entity 106. In a particular embodiment, the client computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the client computing entity 102 may operate in accordance with multiple wired communication standards and protocols, such as those described above with regard to the predictive data analysis computing entity 106 via a network interface 320.

Via these communication standards and protocols, the client computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The client computing entity 102 can also download changes, add-ons, and updates, for instance, to its firmware, software (e.g., including executable instructions, applications, program modules), and operating system.

According to one embodiment, the client computing entity 102 may include location determining aspects, devices, modules, functionalities, and/or similar words used herein interchangeably. For example, the client computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the client computing entity's 102 position in connection with a variety of other systems, including cellular towers, Wi-Fi access points, and/or the like. Similarly, the client computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The client computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the client computing entity 102 to interact with and/or cause display of information/data from the predictive data analysis computing entity 106, as described herein. The user input interface can comprise any of a number of devices or interfaces allowing the client computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the client computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The client computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the client computing entity 102. As indicated, this may include a user application that is resident on the entity or accessible through a browser or other user interface for communicating with the predictive data analysis computing entity 106 and/or various other computing entities.

In another embodiment, the client computing entity 102 may include one or more components or functionality that are the same or similar to those of the predictive data analysis computing entity 106, as described in greater detail above. As will be recognized, these architectures and descriptions are provided for exemplary purposes only and are not limiting to the various embodiments.

In various embodiments, the client computing entity 102 may be embodied as an artificial intelligence (AI) computing entity, such as an Amazon Echo, Amazon Echo Dot, Amazon Show, Google Home, and/or the like. Accordingly, the client computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. Exemplary System Operations

As described below, various embodiments of the present disclosure make important technical contributions to improving predictive accuracy of machine learning models, which in turn improves training speed and training efficiency of machine learning models. It is well-understood in the relevant art that there is typically a tradeoff between predictive accuracy and training speed, such that it is trivial to improve training speed by reducing predictive accuracy, and thus the real challenge is to improve training speed without sacrificing predictive accuracy through innovative model architectures, see, e.g., Sun et al., *Feature-Frequency—Adaptive On-line Training for Fast and Accurate Natural Language Processing* in 40(3) Computational Linguistic 563 at Abst. ("Typically, we need to make a tradeoff between speed and accuracy. It is trivial to improve the training speed via sacrificing accuracy or to improve the accuracy via sacrificing speed. Nevertheless, it is nontrivial to improve the training speed and the accuracy at the same time"). Accordingly, the techniques described herein improve predictive accuracy without harming training speed, such as various techniques described herein, enable improving training speed given a constant predictive accuracy. In doing so, the techniques described herein improve accuracy, efficiency, and speed of machine learning models, thus reducing the number of computational operations needed and/or the amount of training data entries needed to train machine learning models. Accordingly, the techniques described herein improve at least one of the computational efficiency, storage-wise efficiency, and speed of training machine learning models.

FIG. 4 presents a flowchart diagram of an example process 400 for performing classification operations on input data objects comprising sets of temporal sequences. Via the various steps/operations of the process 400, the predictive data analysis computing entity 106 can use a combination of machine learning models to generate one or more predictive classification labels for input data objects associated with a plurality of features.

The process 400 begins at step/operation 402 when the predictive data analysis computing entity 106 identifies (e.g., receives) a plurality of input data objects. In some embodiments, the predictive data analysis computing entity 106 identifies a plurality of input data objects each comprising a temporal sequence of a plurality of temporal sequences with respect to which one or more predictive data analysis operations are performed. For example, a temporal sequence may describe a set of features (e.g., a set of diagnosis codes) associated with a medical visit.

In some embodiments, a temporal sequence describes an input data object comprising a set $$x_t^n = \{d_t\}$$

for each given time t, where n corresponds to a given predictive entity (e.g., a particular patient) and $d_t$ is representative of one or more features of the entity at the given time t. A temporal sequence may comprise images, text files, audio/video files, and application files that may be used to, for example, train a machine learning model. For example, the set associated with a temporal sequence may describe the set of diagnosis codes associated with a patient admission on a given date and the given entity may represent the patient. Features within a temporal sequence may be internally related and include correlations of various degrees that may be interpreted with various meanings.

In some embodiments, a set of temporal sequences describes a plurality of temporal sequences $$E_{1:T-1}^n = \{x_1^n, x_2^n, \ldots, x_{T-1}^n\}$$

of a given entity n for T number of time instances (e.g., dates). In some embodiments, the plurality of temporal sequences may be an ordered set of temporal sequences. As an example, the set of temporal sequences may comprise a patient's EHRs comprising a history of admissions where each of the plurality of temporal sequences may represent an admission within a time series. As such, a set of temporal sequences may be representative of a patient's condition over multiple admissions, procedures, and medications.

In some embodiments, a feature describes an attribute or characteristic associated with an input data object, such as a temporal sequence, that may be used for analysis and training of a machine learning model. As an example, features of an input data object may comprise clinical events including diagnoses, associated symptoms, or medical codes, e.g., International Statistical Classification of Diseases and Related Health Problems (ICD) codes, Current Procedural Terminology (CPT) codes, prescription (RX) codes.

An example of input data objects comprising a plurality of temporal sequences may be a collection of EHR data objects associated with a plurality of patients. The collection of EHR data objects may be used to generate a set of temporal sequences representative of a historical record associated with a given patient. Each temporal sequence may include a series of features associated with a single admission of the given patient, such as clinical events including diagnoses, procedures, medications, etc. In some embodiments, the clinical events may be represented as or associated with ICD codes, CPT codes, and RX codes. As such, an input data object may comprise a plurality of correlated relationships within its features for generating predictions.

At step/operation 404, the predictive data analysis computing entity 106 generates, based at least in part on the input data object, a global guidance correlation graph. A global guidance correlation graph may comprise a graph including nodes that are representative of a universe of features appearing in the input data objects. For example, the nodes of a global guidance correlation graph may include all features in a dataset comprising a plurality of sets of temporal sequences associated with a plurality of entities. The global guidance correlation graph may further include edges that are generated based at least in part on co-occurrence probability between the universe of features. As an example, edges of a global guidance correlation graph may include weights that may be calculated based at least in part on total number of temporal sequences that a feature pair have co-occurred, total number of temporal sequences that features of the pair have appeared at least once, and total number of temporal sequences.

In some embodiments, co-occurrence probability describes a measurement of relationship between two variables. According to various embodiments of the present disclosure, the relationship may comprise a semantic proximity of the two variables. For example, co-occurrence frequency may comprise an above-chance frequency of features coinciding or existing within a body of data. As an example, a plurality of medical admission records may commonly include terms that describe certain comorbidities where there is a simultaneous presence of two or more medical conditions that are often related. As such, co-occurrence probability may reflect a statistical frequency in which certain terms are present within a single admission record.

At step/operation 406, the predictive data analysis computing entity 106 generates dynamic co-occurrence graphs for a given entity based at least in part on the global guidance correlation graph. Generating the dynamic co-occurrence graphs may include extracting temporal sequences from the input data object. According to some embodiments, dynamic co-occurrence graphs may be generated for each temporal sequence of a set of temporal sequences corresponding to the given entity. Dynamic co-occurrence graphs may comprise a plurality of semantic graphs including features associated with a plurality of temporal sequences over time. In some embodiments, a dynamic co-occurrence graph may be constructed based at least in part on global correlations from a global guidance correlation graph. In other words, a dynamic co-occurrence graph may comprise a projection of the global guidance correlation graph on a given temporal sequence.

According to various embodiments of the present disclosure, generating the dynamic co-occurrence graphs may comprise generating a sequence of adjacency matrices representative of a set of temporal sequences associated with a given entity, where each adjacency matrix comprises a fully connected graph including nodes that represent features corresponding to a given temporal sequence of the set of temporal sequences associated with the given entity. The adjacency matrices may further include edges and edge weights based at least in part on a global guidance correlation graph.

An operational example of dynamic co-occurrence graphs is depicted in FIG. 5. As depicted in FIG. 5, each of temporal sequences 502A, 502B, and 502C comprise patient cards representative of an ordered sequence of admissions for a given patient entity. The temporal sequences 502A, 502B, and 502C include one or more features representative of ICD codes. According to embodiments of the present disclosure, the temporal sequences 502A, 502B, and 502C may be processed into a corresponding ordered sequence of dynamic co-occurrence graphs 504A, 504B, and 504C based at least in part on respective one or more features of the temporal sequences 502A, 502B, and 502C.

Returning to FIG. 4, at step/operation 408, the predictive data analysis computing entity 106 generates initial embeddings based at least in part on the input data objects. In some embodiments, an attentional encoder decoder machine learning model processes features from the input data objects to generate the initial embeddings. As an example, generating the initial embeddings may comprise generating, for each temporal sequence within a set of temporal sequences for a given entity, an initial embedding corresponding to a given temporal sequence.

An initial embedding may comprise an initial representation of features from input data objects, where a feature matrix may be generated by processing the input data objects using an attentional encoder decoder machine learning model. For example, an initial embedding may comprise a translation of features from a given temporal sequence to a feature matrix comprising a tree hierarchy using an input embedding module of the attentional encoder decoder machine learning model.

In some embodiments, an attentional encoder decoder machine learning model describes parameters, hyperparameters, and/or defined operations of a machine learning model, where the machine learning model is configured to translate features into a feature matrix by processing input data objects. As described above, the attentional encoder decoder machine learning model may comprise at least an input embedding module that translates features from a temporal sequence to a feature matrix. In some embodiments, the feature matrix may be created by using a tree-of-sequences LSTM network.

In some embodiments, each feature may be associated with a description that describes the semantics of the features. For example, a feature such as a diagnostic code may be associated with a short text description that describes the semantics of the diagnostic code. Other examples of such a description may include metadata or captioning. The descriptions may be extracted from the input data object or retrieved from a data source, e.g., a lookup database.

According to various embodiments of the present disclosure, the input embedding module may include a description encoder that generates a latent representation vector for a description corresponding to a feature. The description encoder may use a sequential LSTM network to encode descriptions of features. The input embedding module may further include a feature encoder that creates a tree-of-sequences LSTM network to capture hierarchal relationships among the features. Each node of the tree-of-sequences LSTM network may comprise an input vector based at least in part on the latent representation generated by the sequential LSTM.

In some embodiments, a LSTM network describes a recurrent neural network that stores a representation of features from sequences of input data objects, such as a set of temporal sequences, where long- and short-term information dependencies are preserved.

In some embodiments, a sequential LSTM network describes a LSTM network that learns a latent representation of features (which may reflect certain semantic information) and models a sequential structure among the features.

In some embodiments, a tree-of-sequences LSTM network describes a hierarchy of sequential LSTM networks. As described above, the tree-of-sequences LSTM network comprises features that are encoded by a sequential LSTM and applying a tree structure to the sequential LSTM to capture hierarchical relationships among the features. Each node of the tree-of-sequences LSTM network may comprise a vector including a latent representation based at least in part on the encoding by the sequential LSTM.

At step/operation 410, the predictive data analysis computing entity 106 generates historical node representations using the initial embeddings based at least in part on the dynamic co-occurrence graphs. In some embodiments, the initial embeddings are provided as input to a graph-attention augmented module. The initial embeddings, for example, may comprise initial representations of features for each of a plurality of temporal sequences within a set of temporal sequences for a given entity. The initial representations may be used by the graph-attention augmented module to build historical node representations based at least in part on adjacency information (e.g., information from node neighbors) from dynamic co-occurrence graphs.

According to various embodiments of the present disclosure, the graph-attention augmented module may generate historical node representations by using a plurality of dynamic co-occurrence graphs to update the initial embeddings over a progression through time corresponding to a set of temporal sequences. Each update to an initial embedding may comprise an encounter-level historical node representation corresponding to each temporal sequence within the set of temporal sequences. The updates may represent, for example, a progression of disease conditions for a patient. As such, a historical node representation may comprise an initial embedding that has been updated based at least in part on a dynamic co-occurrence graph. A historical node representation may be generated for each temporal sequence of a set of temporal sequences for a given entity. Accordingly, one or more of the historical node representations may be aggregated and used to perform predictive actions.

The graph-attention augmented module may comprise a tempo-spatial graph attention model (TSA) that generates the historical node representations using a graph-attention augmented temporal neural network. In some embodiments, a graph-attention augmented temporal neural network describes a two-layer graph-attention neural network for embedding historical node representations. In some embodiments, the graph-attention augmented temporal neural network model may update an initial embedding based at least in part on the dynamic co-occurrence graphs. The graph-attention augmented temporal neural network may construct encoded feature vectors that contain information of other co-occurrence features of a same temporal sequence with different degrees of correlation to obtain more comprehensive representation. As an example, at each embedding layer, the graph-attention augmented temporal neural network can embed a set of historical node representations by recursively aggregating information from node neighbors based at least in part on the dynamic co-occurrence graphs.

In some embodiments, a node representation may comprise a feature vector. According to one embodiment, the historical node feature vector at a l-th graph attention layer $$h^{i}_{\{t,i\}}$$

can be obtained through the following equation:

$$h^{i}_{\{t,i\}} = \sigma\left(\sum_{\{j\in N_i\}} \alpha_{\{ij\}} h^{\{l-1\}}_{\{t,i\}} W^{l} + b^{l}\right) \quad \text{Equation 1}$$

where σ is a non-linear activation function, W and b are learnable parameters, and $N_i$ is the set of neighboring nodes of node i in the graph.

According to one embodiment, for each time step representative of a given temporal sequence, a corresponding initial embedding may be provided to a TSA. The TSA may be trained with the initial embedding based at least in part on adjacency information (e.g., information from node neighbors) of a current temporal sequence of a current time step. The adjacency information may be provided to TSA as a dynamic co-occurrence graph corresponding to a given time step.

An operational example of building historical node representations is depicted in FIG. 6. As depicted in FIG. 6, a sequential series of initial embeddings 602 comprising training progression of initial embeddings of features (diagnostic or ICD codes) is modeled over time to characterize a patient's clinical history. For each time step T representative of a given temporal sequence (e.g., admission), an initial embedding associated with a clinical graph including features (e.g., diagnostic codes) is provided to TSA 606 and is trained with adjacency information 604 of a current temporal sequence of a current time step. The adjacency information may be provided to TSA 606 as a dynamic co-occurrence graph corresponding to a given time step.

According to the illustrated example depicted in FIG. 6, an initial embedding for a time step T=1 is provided to the TSA 606. TSA 606 trains on the initial embedding for time step T=1 based at least in part on adjacency information (e.g., a dynamic co-occurrence graph) corresponding to time step T=1 and generates a historical node representation for time step T=1.

For a next time step T=2, an initial embedding for time step T=2 is provided to the TSA 606. TSA 606 trains on the initial embedding for time step T=2 based at least in part on adjacency information corresponding to time step T=2 and generates a historical node representation for time step T=2. This process is iteratively performed up to time step T=K, which may be representative of a present time temporal sequence (e.g., admission) where the TSA 606 may be used to perform a predictive function based at least in part on training of the initial embeddings with adjacency information over a plurality of time steps. The predictive function may comprise a classification task for predicting future features 608, such as one or more rare disease (e.g., ICD codes) classification labels.

A machine learning framework 700 according to various embodiments of the present disclosure is depicted in FIG. 7. As depicted in FIG. 7, the machine learning framework 700 comprises a plurality of input embedding modules 702A, 702B, . . . 702N. Each of the input embedding modules 702A, 702B, . . . 702N may generate an initial embedding corresponding to a given temporal sequence associated with a corresponding time. The initial embeddings may be provided to the graph-attention augmented modules 704A, 704B, . . . 704N. The initial embeddings may be used for model training by each of the respective graph-attention augmented modules 704A, 704B, . . . 704N to build respective historical node representations based at least in part on adjacency information (e.g., information from node neighbors) from respective dynamic co-occurrence graphs associated with each time T. In one embodiment, the graph-attention augmented modules 704A, 704B, . . . 704N may compute an attention coefficient for determining the importance of each of the neighbor's feature to a given historical node representation. The graph-attention augmented modules 704A, 704B, . . . 704N may be further configured to consider all features appearing in a set of temporal sequences, and embed all historical node representations that have been created up to time T=K to generate a final historical representation.

Temporal dependency updating module 706 may be configured to model temporal evolution of each time step (e.g., temporal sequence) in the historical node representations at different time steps. For example, at each time step, when an initial embedding is updated, the corresponding historical node representation may selectively retain at least a portion of information from previous historical node representations. The temporal dependency updating module 706 may comprehensively capture the features appearing in a set of temporal sequences and generate feature vectors of the historical node representations that have been created to generate a final historical representation. An overall representation matrix may be incrementally generated by temporal dependency updating module 706 which may be transmitted to the classification module 708 to obtain one or more predicted outputs.

Returning to FIG. 4, at step/operation 412, the predictive data analysis computing entity 106 generates a classification based at least in part on the historical node representations. Generating the classification may comprise a prediction including one or more predictive classification labels. According to one embedment, the classification may be generated based at least in part on features of the historical node representations where each node feature integrates the structural and temporal characteristics of the dynamic co-occurrence graphs. In one embodiment, the features from each historical node representation may be combined and used to generate a final prediction. In another embodiment, the classification may comprise a multi-instance multi-label classification task. For example, the classification may comprise a plurality of predictions including one or more classification labels for each time step corresponding to a plurality of historical node representations (e.g., temporal sequences associated with a set of temporal sequences).

In some embodiments, a classification label describes descriptions, tags, or identifiers that classify or emphasize features present in a body of data. In some embodiments, a predictive classification label describes a prediction output of a machine learning model, such as a graph-attention augmented temporal neural network model. The prediction output may comprise a classification output including one or more classification labels based at least in part on a given input data object. As an example, in some embodiments, the classification labels may comprise medical codes, e.g., ICD codes, CPT codes, and RX codes that are generated as classification output for prediction on a set of temporal sequences. According to various embodiments of the present disclosure, a predictive classification label may comprise a diagnostic code for a rare disease $y_t=\{0,1\}^{L+1}$, where L is the number of rare diseases considered, and all other diseases are represented as a single binary vector.

According to some embodiments, generating the classification may comprise minimizing a loss function for optimizing the performance of the classification. For example, the loss function may be modeled as follows:

$$\mathcal{L} = \frac{1}{T-1}\sum_{\{t=2\}}^{T}\left(y_t^T\log(\hat{y}_t^T) + \left(1-y_t^T\right)\log\left(1-\hat{y}_t^T\right)\right), \quad \text{Equation 2}$$

where $$y_t^T$$

is the ground truth vector and $$\hat{y}_t^T$$

is the output predicted by the output at time instant t. An algorithm, such as the Adam optimizer may be employed to minimize the loss function above.

At step/operation 414, the predictive data analysis computing entity 106 performs one or more prediction-based actions based at least in part on the classification. In some embodiments, performing the one or more prediction-based actions comprises performing one or more appointment scheduling operations and generating corresponding messages that are transmitted to client devices via an electronic communication system where the messages are rendered on one or more user interfaces. In another embodiment, performing the one or more prediction-based actions comprises generating one or more automated investigation operations and rendering a diagnosis on a user interface. In yet another embodiment, performing the one or more prediction-based actions comprises generating one or more automated audit operations based at least in part on the classification and rendering results of the one or more automated audit operations on a user interface. In some embodiments, performing the one or more prediction-based actions based at least in part on the classification includes generating one or more diagnostic codes for rare diseases on a prediction output user interface on a computing device.

Accordingly, as described above, various embodiments of the present disclosure make important technical contributions to improving predictive accuracy of machine learning models, which in turn improves training speed and training efficiency of machine learning models. It is well-understood in the relevant art that there is typically a tradeoff between predictive accuracy and training speed, such that it is trivial to improve training speed by reducing predictive accuracy, and thus the real challenge is to improve training speed without sacrificing predictive accuracy through innovative model architectures, see, e.g., Sun et al., *Feature-Frequency—Adaptive On-line Training for Fast and Accurate Natural Language Processing* in 40(3) Computational Linguistic 563 at Abst. ("Typically, we need to make a tradeoff between speed and accuracy. It is trivial to improve the training speed via sacrificing accuracy or to improve the accuracy via sacrificing speed. Nevertheless, it is nontrivial to improve the training speed and the accuracy at the same time"). Accordingly, the techniques described herein improve predictive accuracy without harming training speed, such as various techniques described herein, enable improving training speed given a constant predictive accuracy. In doing so, the techniques described herein improve accuracy, efficiency, and speed of machine learning models, thus reducing the number of computational operations needed and/or the amount of training data entries needed to train machine learning models. Accordingly, the techniques described herein improve at least one of the computational efficiency, storage-wise efficiency, and speed of training machine learning models.

Furthermore, various embodiments of the present disclosure improve accuracy of machine learning models by pre-training models with features (e.g., clinical events) based at least in part on textual content as well as hierarchical structure among the features. As described herein, a collection of information, such as an electronic health record ("EHR"), may comprise a large number of features associated with a temporal structure. Existing methods for performing a prediction on a collection of information may include building a prediction model based at least in part on the features and making a prediction. However, existing methods are limited in their abilities in dealing with complex structural correlations and temporal dependencies of features in a temporal sequence (e.g., admission), which may impact classification predictions as well as temporal prediction of classification labels.

However, in accordance with various embodiments of the present disclosure, a temporal-spatial approach may be used to capture temporal feature set (e.g., health) progression as well as relationships among different features over a period. This technique will lead to higher accuracy of performing predictions on input comprising a temporal sequence. In doing so, the techniques described herein improving efficiency and speed of training natural language processing machine learning models, thus reducing the number of computational operations needed and/or the amount of training data entries needed to train machine learning models. Accordingly, the techniques described herein improve at least one of the computational efficiency, storage-wise efficiency, and speed of training machine learning models.

VI. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A computer-implemented method comprising:

receiving, by one or more processors, a set of one or more input data objects, wherein an input data object of the set of one or more input data objects comprises a temporal sequence of a plurality of temporal sequences and a subset of a set of one or more features that corresponds to the set of one or more input data objects;

generating, by the one or more processors, a global guidance correlation graph data object, wherein:

(i) a node of the global guidance correlation graph data object corresponds to a feature of the set of one or more features, and (ii) an edge of the global guidance correlation graph data object (a) corresponds to a feature pair of the set of one or more features, and (b) comprises a weight that corresponds to a co-occurrence probability for the feature pair;

generating, by the one or more processors, a set of one or more dynamic co-occurrence graph data objects based at least in part on the global guidance correlation graph data object, wherein a dynamic co-occurrence graph data object of the set of one or more dynamic co-occurrence graph data objects (i) corresponds to the temporal sequence and (ii) comprises a projection of the global guidance correlation graph data object on the input data object that corresponds to the temporal sequence;

generating, by the one or more processors and using a set of one or more embeddings, a set of one or more historical node representations based at least in part on the set of one or more dynamic co-occurrence graph data objects, wherein the set of one or more embeddings is:

(i) generated by:

(a) generating a set of one or more latent representation vectors that correspond to a set of one or more descriptions of the subset of the set of one or more features, and (b) generating, based at least in part on the set of one or more latent representation vectors, a set of one or more input vectors that correspond to one or more hierarchical relationships between the subset of the set of one or more features, and (ii) modified over a progression through time corresponding to the set of one or more dynamic co-occurrence graph data objects;

providing, by the one or more processors, the set of one or more historical node representations to a machine learning model to produce a set of one or more predicted classification labels, wherein accuracy of the machine learning model is improved by using the set of one or more embeddings to generate a set of one or more training historical node representations that corresponds to one or more model parameters of the machine learning model.

2. The computer-implemented method of claim 1, wherein:

(i) an edge of the set of one or more dynamic co-occurrence graph data objects for the temporal sequence is associated with the feature pair, and (ii) the feature pair is in a related feature subset for the temporal sequence.

3. The computer-implemented method of claim 1, wherein an initial embedding for the feature is generated based at least in part on a latent representation of text data associated with the feature and a hidden representation for one or more related features that corresponds to the feature as defined by a classification tree of a tree-of-sequences long short-term memory machine learning model.

4. The computer-implemented method of claim 1, wherein the set of one or more predicted classification labels are generated based at least in part on a hidden state that is generated based at least in part on a historical node representation of the set of one or more historical node representations that corresponds to a related feature subset of a final temporal sequence.

5. The computer-implemented method of claim 1, wherein:

the dynamic co-occurrence graph data object comprises a sequence of adjacency matrices.

6. The computer-implemented method of claim 1, wherein a historical node representation h of the set of one or more historical node representations that corresponds to (a) a temporal sequence t of the plurality of temporal sequences, (b) a non-initial embedding layer l, and (c) a feature i, is generated based at least in part on $$h^{i}_{\{t,i\}} = \sigma\left(\sum_{\{j \in N_i\}} \alpha_{\{ij\}} h^{\{l-1\}}_{\{t,i\}} W^{l} + b^{l}\right),$$

where $\sigma$ comprises a non-linear activation function, W and b comprise learnable parameters, and $N_i$ comprises a set of one or more neighbor nodes for a target node associated with the feature i in the dynamic co-occurrence graph data object that corresponds to the temporal sequence t.

7. The computer-implemented method of claim 1, wherein the co-occurrence probability for the feature pair describes a count of co-occurrences of the feature pair in a common temporal sequence across the set of one or more input data objects.

8. A system comprising one or more processors; and one or more memories storing processor-executable instructions that, when executed by the one or more processors, cause the one or more processors to perform operations comprising:

receiving a set of one or more input data objects, wherein an input data object of the set of one or more input data objects comprises a temporal sequence of a plurality of temporal sequences and a subset of a set of one or more features that corresponds to the set of one or more input data objects;

generating a global guidance correlation graph data object, wherein:

(i) a node of the global guidance correlation graph data object corresponds to a feature of the set of one or more features, and (ii) an edge of the global guidance correlation graph data object (a) corresponds to a feature pair of the set of one or more features, and (b) comprises a weight that corresponds to a co-occurrence probability for the feature pair;

generating a set of one or more dynamic co-occurrence graph data objects based at least in part on the global guidance correlation graph data object, wherein a dynamic co-occurrence graph data object of the set of one or more dynamic co-occurrence graph data objects (i) corresponds to the temporal sequence and (ii) comprises a projection of the global guidance correlation graph data object on the input data object that corresponds to the temporal sequence;

generating, using a set of one or more embeddings, a set of one or more historical node representations based at least in part on the set of one or more dynamic co-occurrence graph data objects, wherein the set of one or more embeddings is:

(i) generated by:

(a) generating a set of one or more latent representation vectors that correspond to a set of one or more descriptions of the subset of the set of one or more features, and (b) generating, based at least in part on the set of one or more latent representation vectors, a set of one or more input vectors that correspond to one or more hierarchical relationships between the subset of the set of one or more features, and (ii) modified over a progression through time corresponding to the set of one or more dynamic co-occurrence graph data objects;

providing the set of one or more historical node representations to a machine learning model to produce a set of one or more predicted classification labels, wherein accuracy of the machine learning model is improved by using the set of one or more embeddings to generate a set of one or more training historical node representations that corresponds to one or more model parameters of the machine learning model.

9. The system of claim 8, wherein:
(i) an edge of the set of one or more dynamic co-occurrence graph data objects for the temporal sequence is associated with the feature pair, and
(ii) the feature pair is in a related feature subset for the temporal sequence.

10. The system of claim 8, wherein an initial embedding for the feature is generated based at least in part on a latent representation of text data associated with the feature and a hidden representation for one or more related features that corresponds to the feature as defined by a classification tree of a tree-of-sequences long short-term memory machine learning model.

11. The system of claim 8, wherein the set of one or more predicted classification labels are generated based at least in part on a hidden state that is generated based at least in part on a historical node representation of the set of one or more historical node representations that corresponds to a related feature subset of a final temporal sequence.

12. The system of claim 8, wherein:
the dynamic co-occurrence graph data object comprises a sequence of adjacency matrices.

13. The system of claim 8, wherein a historical node representation h of the set of one or more historical node representations that corresponds to (a) a temporal sequence t of the plurality of temporal sequences, (b) a non-initial embedding layer l, and (c) a feature i, is generated based at least in part on $$h^{l}_{\{t,i\}} = \sigma\left(\sum_{\{j \in N_i\}} \alpha_{\{ij\}} h^{(l-1)}_{\{t,i\}} W^{l} + b^{l}\right),$$

where σ comprises a non-linear activation function, W and b comprise learnable parameters, and $N_i$ comprises a set of one or more neighbor nodes for a target node associated with the feature i in the dynamic co-occurrence graph data object that corresponds to the temporal sequence t.

14. The system of claim 8, wherein the co-occurrence probability for the feature pair describes a count of co-occurrences of the feature pair in a common temporal sequence across the set of one or more input data objects.

15. One or more non-transitory computer-readable media storing processor-executable instructions that, when executed by one or more processors, cause the one or more processors to perform operations comprising:
receiving a set of one or more input data objects, wherein an input data object of the set of one or more input data objects comprises a temporal sequence of a plurality of temporal sequences and a subset of a set of one or more features that corresponds to the set of one or more input data objects;
generating a global guidance correlation graph data object, wherein:
(i) a node of the global guidance correlation graph data object corresponds to a feature of the set of one or more features, and
(ii) an edge of the global guidance correlation graph data object (a) corresponds to a feature pair of the set of one or more features, and (b) comprises a weight that corresponds to a co-occurrence probability for the feature pair;
generating a set of one or more dynamic co-occurrence graph data objects based at least in part on the global guidance correlation graph data object, wherein a dynamic co-occurrence graph data object of the set of one or more dynamic co-occurrence graph data objects (i) corresponds to the temporal sequence and (ii) comprises a projection of the global guidance correlation graph data object on the input data object that corresponds to the temporal sequence;
generating, using a set of one or more embeddings, a set of one or more historical node representations based at least in part on the set of one or more dynamic co-occurrence graph data objects, wherein the set of one or more embeddings is:
(i) generated by:
(a) generating a set of one or more latent representation vectors that correspond to a set of one or more descriptions of the subset of the set of one or more features, and
(b) generating, based at least in part on the set of one or more latent representation vectors, a set of one or more input vectors that correspond to one or more hierarchical relationships between the subset of the set of one or more features, and
(ii) modified over a progression through time corresponding to the set of one or more dynamic co-occurrence graph data objects;
providing the set of one or more historical node representations to a machine learning model to produce a set of one or more predicted classification labels, wherein accuracy of the machine learning model is improved by using the set of one or more embeddings to generate a set of one or more training historical node representations that corresponds to one or more model parameters of the machine learning model.

16. The one or more non-transitory computer-readable media of claim 15, wherein:
(i) an edge of the set of one or more dynamic co-occurrence graph data objects for the temporal sequence is associated with the feature pair, and
(ii) the feature pair is in a related feature subset for the temporal sequence.

17. The one or more non-transitory computer-readable media of claim 15, wherein an initial embedding for the feature is generated based at least in part on a latent representation of text data associated with the feature and a hidden representation for one or more related features that corresponds to the feature as defined by a classification tree of a tree-of-sequences long short-term memory machine learning model.

18. The one or more non-transitory computer-readable media of claim 15, wherein the set of one or more predicted classification labels are generated based at least in part on a hidden state that is generated based at least in part on a historical node representation of the set of one or more historical node representations that corresponds to a related feature subset of a final temporal sequence.

19. The one or more non-transitory computer-readable media of claim 15, wherein:
the dynamic co-occurrence graph data object comprises a sequence of adjacency matrices.

20. The one or more non-transitory computer-readable media of claim 15, wherein a historical node representation h of the set of one or more historical node representations that corresponds to (a) a temporal sequence t of the plurality of temporal sequences, (b) a non-initial embedding layer l, and (c) a feature i, is generated based at least in part on $$h^{l}_{\{t,i\}} = \sigma\left(\sum_{\{j \in N_i\}} \alpha_{\{ij\}} h^{(l-1)}_{\{t,i\}} W^{l} + b^{l}\right),$$

where σ comprises a non-linear activation function, W and b comprise learnable parameters, and $N_i$ comprises a set of one or more neighbor nodes for a target node associated with the feature i in the dynamic co-occurrence graph data object that corresponds to the temporal sequence t.

* * * * *